(12) United States Patent
Auberger et al.

(10) Patent No.: US 8,083,807 B2
(45) Date of Patent: Dec. 27, 2011

(54) METHOD FOR ADJUSTING A LEG PROSTHESIS AND VERIFYING THE ADJUSTMENT, AND APPARATUS FOR THE MEASUREMENT OF FORCES OR MOMENTS IN A LEG PROSTHESIS

(75) Inventors: Roland Auberger, Vienna (AT); Martin Pusch, Duderstadt (DE)

(73) Assignee: Otto Bock Healthcare GmbH, Duderstadt (DE)

( * ) Notice: Subject to any disclaimer, the term of this patent is extended or adjusted under 35 U.S.C. 154(b) by 812 days.

(21) Appl. No.: 12/091,497

(22) PCT Filed: Oct. 25, 2006

(86) PCT No.: PCT/DE2006/001909
§ 371 (c)(1),
(2), (4) Date: Apr. 25, 2008

(87) PCT Pub. No.: WO2007/048404
PCT Pub. Date: May 3, 2007

(65) Prior Publication Data
US 2008/0288086 A1  Nov. 20, 2008

(30) Foreign Application Priority Data
Oct. 26, 2005 (DE) .......................... 10 2005 051 646

(51) Int. Cl.
*A61B 5/11* (2006.01)
*A61F 2/64* (2006.01)
(52) U.S. Cl. ........................... 623/39; 623/40; 73/865.4
(58) Field of Classification Search ........ 73/862.041–862.045, 865.4; 623/20.14–20.36, 39–47
See application file for complete search history.

(56) References Cited

U.S. PATENT DOCUMENTS 3,273,168 A * 9/1966 Gardner et al. ................. 623/38
(Continued)

FOREIGN PATENT DOCUMENTS

DE    101 39 333 A1    3/2003
(Continued)

OTHER PUBLICATIONS

Article: "Moglichkeiten zur Optimierung der prothetischen Versorgung Beinamputierter mittels quantitativer Bewegunsanalyse", Biomedizinische Technik, vol. 38, No. 6, Jun. 1, 1993, pp. 144-152, Xpooo369834 Schiele Und Schoen GmbH Berlin, DE ISSN: 0013-5585 "Possibilities for the Optimization of Lower Limb Prosthetics by Gait Analysis" with abstract in English.
(Continued)

*Primary Examiner* — Lisa Caputo
*Assistant Examiner* — Jonathan Dunlap
(74) *Attorney, Agent, or Firm* — Holland & Hart, LLP (57) ABSTRACT

A method is provided for verifying the adjustment of a leg prosthesis. The leg prosthesis includes a prosthetic knee joint pivotally connected to an upper connection and a lower leg shaft. The upper connection fixes the leg prosthesis on a user of the leg prosthesis and the lower leg shaft fastens to a prosthetic foot. The upper connection is displaceable in relation to a joint axis of the prosthetic knee joint. The method includes measuring a knee moment and an axial force by means of sensors when leg prosthesis is being used; calculating a resultant force vector using the knee moment and the axial force; calculating a normal distance relative to the joint axis and the position of the resultant force vector in relation to the joint axis; and verifying a position of the resultant force vector relative to the joint axis in the sagittal plane.

27 Claims, 9 Drawing Sheets

U.S. PATENT DOCUMENTS

| | | | |
|---|---|---|---|
| 3,538,516 A * | 11/1970 | Gregory et al. | 623/38 |
| 4,608,054 A * | 8/1986 | Schroder | 623/39 |
| 4,883,494 A * | 11/1989 | Cooper | 623/39 |
| 5,181,931 A * | 1/1993 | van de Veen | 623/40 |
| 6,033,440 A * | 3/2000 | Schall et al. | 623/38 |
| 6,231,618 B1 * | 5/2001 | Schall et al. | 623/38 |
| 6,458,163 B1 * | 10/2002 | Slemker et al. | 623/38 |
| 7,338,532 B2 * | 3/2008 | Haberman et al. | 623/38 |
| 7,500,407 B2 * | 3/2009 | Boiten | 73/862.191 |
| 2005/0166685 A1 * | 8/2005 | Boiten | 73/862.191 |
| 2005/0283257 A1 * | 12/2005 | Bisbee et al. | 623/24 |
| 2006/0136072 A1 * | 6/2006 | Bisbee et al. | 623/24 |
| 2008/0276725 A1 * | 11/2008 | Pusch | 73/862.041 |

FOREIGN PATENT DOCUMENTS

| | | |
|---|---|---|
| EP | 1 285 640 A2 | 2/2003 |
| EP | 1 559 384 A1 | 8/2005 |
| GB | 1 208 421 | 10/1970 |
| WO | 96/00540 | 1/1996 |

OTHER PUBLICATIONS

International Search Report for PCT/D2006/001909 dated May 24, 2007, 3 pgs.

* cited by examiner

METHOD FOR ADJUSTING A LEG PROSTHESIS AND VERIFYING THE ADJUSTMENT, AND APPARATUS FOR THE MEASUREMENT OF FORCES OR MOMENTS IN A LEG PROSTHESIS

CROSS-REFERENCE TO RELATED APPLICATION

This patent application is a national stage application of International Application No. PCT/DE2006/0019090 filed Oct. 25, 2006, which claims priority to German Patent Application No. 10 2005 051 646.7, filed on Oct. 26, 2005. The entire content of these applications are hereby expressly incorporated by reference.

TECHNICAL FIELD

The invention relates to a method for adjusting a leg prosthesis and for verifying the adjustment. The prosthesis has a prosthetic knee joint pivotally connecting an upper connection for fixing the leg prosthesis on a user of the prosthesis, in particular an upper leg shaft, and a lower leg shaft to which a prosthetic foot can be fastened. The upper connection is displaceable in relation to a joint axis. The invention likewise relates to an apparatus for determining forces and moments in a leg prosthesis, for example a hip exarticulation prosthesis or upper leg prosthesis.

BACKGROUND

The relative position between an upper leg shaft and the actual prosthetic knee joint is of central importance for the functionality and comfort of the prosthesis fitting. This relative position has a strong influence on the stability of the prosthesis with respect to unintended bending of the prosthesis when standing and on the reaction forces between the upper leg shaft and the limb of the upper leg. Particularly important is aligning the prosthesis in the sagittal plane, which is also described as "setup".

In every prosthesis setup, a compromise has to be found between adequate stability during standing and the least possible expenditure of force during walking. The greater the stability during standing, the greater the expenditure of force during walking. If the expenditure of force during walking is minimized, an unstable setup of the prosthetic knee joint may occur, which has to be compensated by active use of the hip musculature. This is disadvantageous for the user of the prosthesis.

The stability during standing is achieved in principle by setting back the prosthetic knee joint or the joint axis in relation to the upper leg shaft. This ensures that the weight vector of the prosthesis user originating from the body extends in front of the joint axis of the prosthetic knee joint during standing, whereby the prosthesis remains in the extended position.

During a step, the prosthesis is intended to bend into the swing phase, for which purpose the weight force vector must extend behind the joint axis of the prosthetic knee joint. This is achieved by the prosthesis user introducing a hip moment. As stated above, the physical force to be applied for this purpose depends greatly on the setup of the prosthetic knee joint. If the setup is too stable, initiation in the swing phase involves great expenditure of force. This leads to premature tiring or to pain in the limb of the upper leg.

At present, the positioning of the prosthetic knee joint in relation to the upper leg shaft takes place statically and on the basis of empirical values. Dynamic effects, such as for example the deformation of the system or of the upper leg during walking, are not taken into account.

DE 101 39 333 A1 describes a sensor device and a prosthesis with a sensor device in which the sensor device is arranged in a part of the shinbone below an artificial knee joint. The sensor device provides an outer body, formed as a closed ring, and an inner body, connecting two opposite inner sides of the outer body and having a sensor element for measuring the force acting in the direction of the connecting axis. Ground reaction forces for analyzing walking can be determined by the sensor device.

SUMMARY

The object of the present invention is to provide methods and an apparatus for a prosthesis setup that improves an upper leg prosthesis and, in particular, for determining and adjusting a favorable prosthesis setup for the standing phase of walking.

The method includes adjusting a leg prosthesis having a prosthetic knee joint pivotally connecting an upper connection for fixing the leg prosthesis on a user of the prosthesis and a lower leg shaft to which a prosthetic foot is fastened. The upper connection is displaceable in relation to a joint axis of the prosthetic knee joint and/or the position of the prosthetic foot in relation to the lower leg shaft. The method includes measuring a knee moment and an axial force by means of sensors when a prosthesis is being used. The knee moment and the axial force are used to calculate a resultant force vector. The normal distance in relation to the joint axis and the position of the resultant force vector in relation to the joint axis are calculated to verify whether and to what extent the resultant force vector lies in front of or behind the joint axis in the sagittal plane. An adjustment of the upper connection in relation to the axis of the prosthetic knee joint and/or extension stops for the prosthetic knee joint and/or a prosthetic foot joint is performed depending on the determined position of the resultant force vector.

The apparatus according to the invention is used for measuring forces or moments in a leg prosthesis, in particular in an upper leg prosthesis or hip exarticulation prosthesis. The apparatus is a prosthetic knee joint for adjusting a prosthesis setup and/or verifying adjustment and includes an upper part for the connection to an upper connection, in particular an upper leg shaft, a lower part jointly connected to the upper part and connecting means for fastening the upper part to the upper connection. The connecting means preferably has an adapter mounted displaceably in the sagittal plane on the upper part and devices for detecting knee forces or knee moments on the connecting means or on the upper part. The apparatus makes it possible to detect the effective forces and moments within a prosthetic knee joint and, in addition, to determine or change the position of the joint axis in relation to the upper leg shaft so that an optimum prosthesis setup can be achieved, preferably by adjusting the connecting means. The adapter may in this case be fixed on the upper part by means of a clamping device. As an alternative, adjusting screws that are accessible from the outside may be provided, for example in the form of a spindle, by means of which the joint axis can be comfortably displaced in relation to the upper part or the upper connection such that prosthesis setup changes and the findings thereby obtained concerning the prosthesis setup can be directly verified in practice.

BRIEF DESCRIPTION OF THE DRAWINGS

An exemplary embodiment of the invention is explained in more detail below on the basis of the figures, in which:

FIG. 7 shows a schematic representation of the restoration of the plantar flexion;

DETAILED DESCRIPTION

Figure 1:
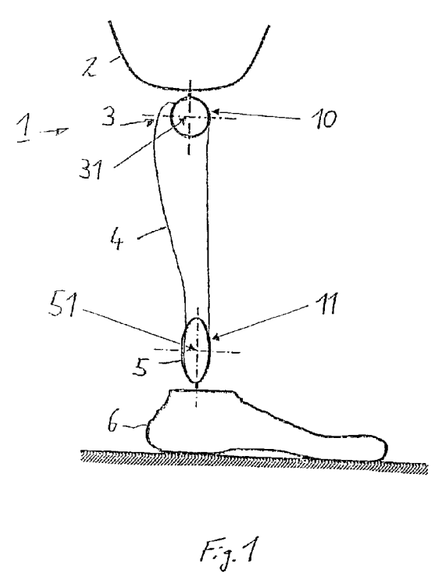
FIG. 1 shows a schematic representation of a leg prosthesis with sensors arranged in it.

Represented in FIG. 1 is a leg prosthesis 1 having an upper leg shaft 2, a knee joint 3 and a lower leg shaft 4. The upper leg shaft 2 can be fastened to a limb of an upper leg (not shown). The knee joint 3 is fastened to the upper leg shaft 2 and is pivotally mounted about a knee axis 31. An osseointegrated upper connection, which connects the knee joint 3 to the limb of the upper leg, may be provided as an alternative to the upper leg shaft 2. In the case of hip exarticulations, there is no limb, so the connection from the knee joint 3 to the hip joint is regarded as the upper connection. The lower leg shaft 4 is fastened to the prosthetic knee joint 3 and connects the knee joint 3 to a prosthetic foot 6 by means of a coupling point 5. The method according to the invention includes measuring a knee moment $M_K$ and an axial force $F_{AX}$ acting in the lower leg shaft 4 by means of sensors when the prosthesis 1 is being used. The sensors are preferably arranged in the prosthetic knee joint 3 and in the lower leg shaft 4. For example, a sensor 10 is provided in the knee joint 3 for measuring the knee moment $M_K$. The measuring axis 31 of the sensor 10 corresponds to the joint axis 31 of the knee joint 3. The knee angle $\phi$ can be determined either by the sensor 10 or another sensor, for example a sensor in the lower leg shaft 4.

In order to take into account the dynamic effects of the upper leg prosthesis 1 during use when determining and optimizing the setup, the knee moment $M_K$ and the axial force $F_{AX}$, and optionally also the ankle moment $M_H$, are measured during walking to determine the knee moment $M_T$ or the resultant force vector based on a force and moment analysis over the length of the step so that a statement as to whether the setup is stable or unstable can be made at any time during walking. The sensor data can be used to determine an axial force $F_{AX}$, a knee moment $M_K$ and an ankle moment $M_T$, from which in turn the vector of the ground reaction force in the sagittal plane is determined. In this way it is possible to determine the stability of the setup of the prosthesis 1 in the standing phase during walking while also taking into account dynamic effects in the evaluation of the prosthesis setup.

The knee moment $M_K$ and the axial force $F_{AX}$ are used to calculate a resultant force vector and the distance of the force vector from the joint axis or the knee axis 31 normal to the axial force $F_{AX}$. The force vector may have a point of attack on the upper connection. The normal distance in relation to the longitudinal axis of the prosthesis 1, which has the same direction as the axial force $F_{AX}$, and the position or orientation of the resultant force vector in relation to the joint axis 31 are calculated and it is verified based on the normal distance whether and to what extent the resultant force vector lies in front of or behind the joint axis 31 in the sagittal plane. If the resultant force vector lies in front of the joint axis 31, the knee joint 3 is stable. If the resultant force vector lies behind the joint axis 31, the knee joint 3 is referred to as an unstable joint. The furthest posterior lying force vector in the course of a step cycle is also determined in order to be able to observe the most unstable situation that occurs in the course of the step cycle. Apart from distinguishing between a stable situation and an unstable situation, it is also possible to make statements about the degree of instability. Here, it is assumed overall that the force vector extends parallel to the axial force $F_{AX}$, which is predominantly the case in prosthetics.

For better visualization of the results in a system of inertial coordinates and an exact assignment of the respective values to the phases of a step, the resultant force vector is determined by determining the current knee angle $\phi$, for example by means of a knee angle sensor or an upper leg angle sensor, which determine the absolute angles in relation to a vertical line. With a known upper leg angle $\phi$, a conversion can be made from a system of coordinates that is fixed for the prosthesis into a system of inertial coordinates. However, it is sufficient for the setup analysis to consider a system of coordinates that is fixed for the prosthesis 1, which can be carried out without taking into account the current knee angle $\phi$ since it is possible to identify the swing phase by determining axial force $F_{AX}$. If the axial force value $F_{AX}$ is zero or if tensile forces are measured instead of compressive forces, it is to be assumed that a swing phase is occurring. In particular, the knee angle $\phi$ may be used for estimating the hip moment $M_H$.

The ankle moment $M_T$ between a prosthetic foot 6 and the lower leg shaft 4 is detected by means of an ankle moment sensor 11 arranged in the connecting region between the lower leg shaft 4 and the prosthetic foot 6. The measuring axis 51 of the sensor 11 lies parallel to the knee axis 31. The ankle moment $M_T$ and the length of the lower leg shaft 4 are used for measuring an effective axial force $F_{AX}$ or resultant force vector within the lower leg shaft 4 and the ankle moment $M_T$. This makes it possible to include a horizontal component of a ground reaction force in the calculation of the position of the resultant force vector. The point of force attack of the resultant force vector on the foot 6 can in this case be calculated from the quotient of the ankle moment $M_T$ and the axial force $F_{AX}$ in the lower leg shaft 4. This allows determination of the position of the force vector even when the axial force $F_{AX}$ is not in parallel alignment with the force vector, allowing increased precision to be achieved in the calculation.

Figure 2:
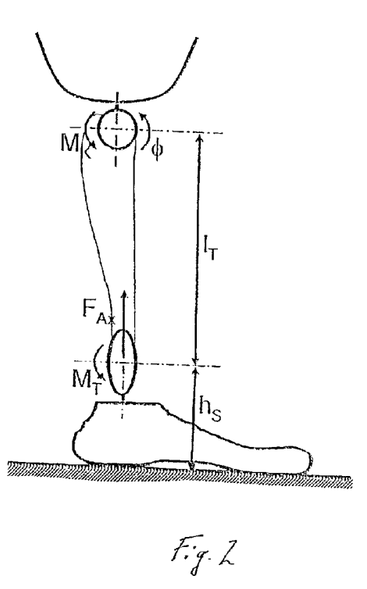
FIG. 2 shows a representation of the effective forces in an arrangement according to FIG. 1.

The heights and lengths as well as the orientations of the forces and moments are shown in FIG. 2. The height of the ankle moment sensor 11 or the sensor axis 51 is denoted by $H_S$.

The distance of the knee axis 31 from the measuring axis 51 of the ankle moment sensor 11 is denoted by $L_T$. Similar to the knee moment $M_K$, the ankle moment $M_T$ is shown positively in the counterclockwise direction, acting upward in the same way as the axial force $F_{AX}$ in the lower leg shaft 4, that is, it is assumed to be positive in the direction of the knee joint 3.

Figure 3:
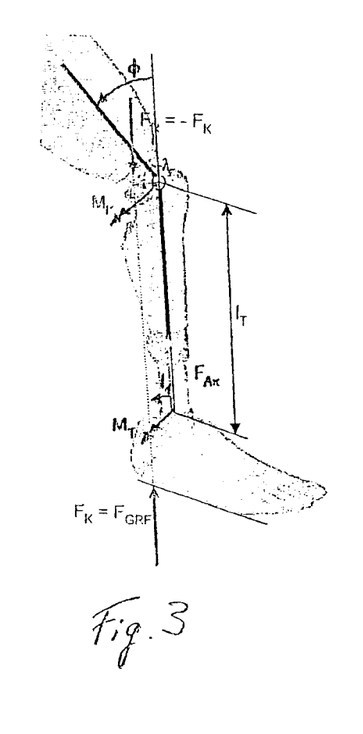
FIG. 3 shows a perspective representation of the moments and relative forces as well as angles.

In FIG. 3, further effective forces are shown in a perspective representation. The contact force $F_K$ is assumed to be the ground reaction force $F_{GRF}$, which is always regarded as being positively effective in the y direction, according to the system of coordinates in FIG. 4. If the upper leg shaft 2 is pivoted counterclockwise by an angle $\phi$, a resultant force $F_R$ acts counter to the contact force $F_K$. The distance $\lambda$, as the normal distance of the force vector $F_R$ from the knee axis 31, is an indicator of whether the setup at a given time of the prosthetic knee joint 3 is stable or unstable. The information indicated by the model applies to any system of coordinates that is considered, such as a system of coordinates that is fixed with respect to the lower leg. If an appraisal of the conditions at the hip is not required or is not of interest, no knee angle information is required.

Figure 4:
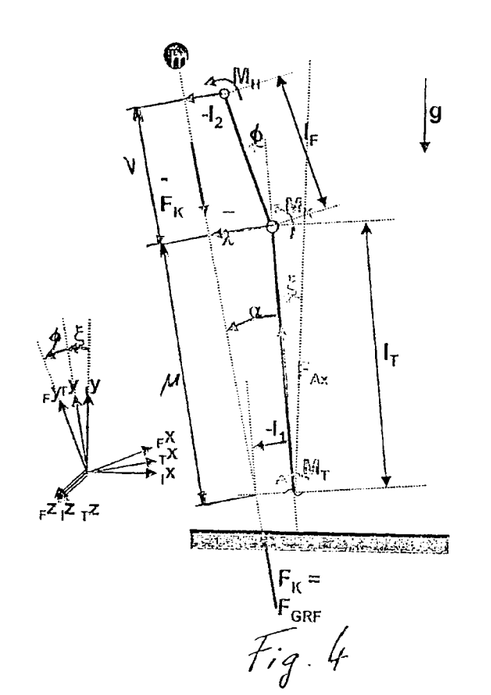
FIG. 4 shows a schematic representation of FIG. 3.

In the situation represented in FIG. 4 of the heel touching down with an angle between the longitudinal axis of the prosthesis 1 and the vertical axis, λ, is negative, so the resultant force vector $F_R$ in the sagittal plane lies behind the joint axis 31. The prosthetic knee joint 3 would consequently be unstable. To be able to provide a stable prosthesis setup, the joint axis 31 would have to be displaced in the negative x direction in the sagittal plane. A set-back displacement of the joint axis 31 consequently has a significant influence on the variations of the knee moment $M_K$, ankle moment $M_T$ and axial force $F_{AX}$.

In the case of a stable prosthesis setup, the knee moment $M_K$ at any given point in time during standing should depend linearly on the set-back displacement on account of the mechanics present, such as the lever lengths. If the prosthesis setup is very unstable, the prosthesis user must actively prevent the prosthesis 1 from bending away from under him by applying a hip extension moment. In theory, this acts as a reduction of the maximum knee moment $M_K$ in the standing phase. In principle, the prosthesis 1 should be set up in such a way that during standing, flexion is possible because impact on contact when the prosthesis 1 is placed on the ground is reduced as a result. For this reason, the prosthesis setup should not be set back too far in order to permit a certain bending moment, but without forcing the prosthesis user to actively prevent further bending of the prosthesis 1. However, the prosthesis setup should cater for the individual wishes of the prosthesis user. The permissible flexion moment during standing is subject to highly individual differences, which are also subject to dynamic influences, so the optimum alignment of the joint axis 31 generally cannot be obtained by carrying out alignment in the static state in the way currently determined by laborious series of tests. This adjusting procedure can be significantly curtailed by the method according to the invention and the apparatus according to the invention.

Figure 5:
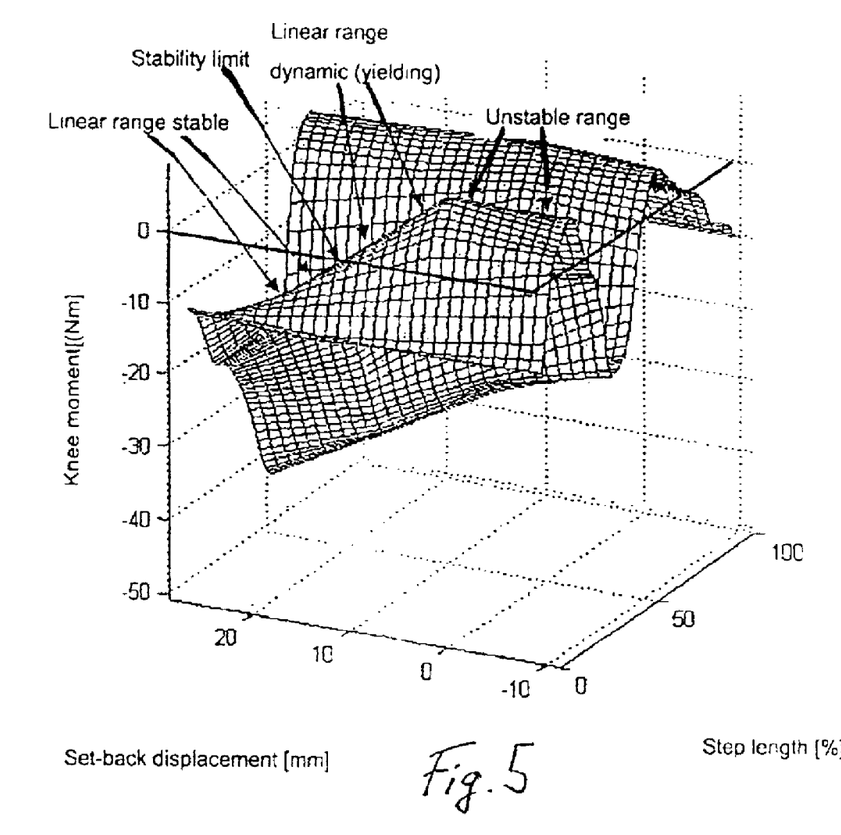
FIG. 5 shows the relationship between the variation of the knee moment and a set-back displacement.

Shown by way of example in FIG. 5 is the relationship between the variation of the knee moment $M_K$ and a set-back displacement over a step cycle. The time is normalized here as a percentual step length with 100% corresponding to a full step cycle. Represented in millimeters on the second horizontal axis is the set-back displacement of the joint axis 31 with respect to an assembly reference line from the middle of the lower leg shaft 4 to the middle of the prosthetic foot 6. A knee moment $M_K$ value of zero marks the transition from a stable prosthesis setup to an unstable prosthesis setup. With a positive knee moment $M_K$, an unstable prosthesis setup is achieved. With a transition from a stable setup to an unstable setup, a stability limit is reached, resulting in a sensible guide value for the adjustment of the prosthesis setup from the standing flexion. If the position of this stability limit is known, it is easy to cater to the individual needs of a prosthesis user by displacing the prosthesis back in a desired stable setup. With a desired dynamic setup, a set-forward displacement can take place.

A further parameter influencing the stability of the prosthesis setup is the pointed foot adjustment. The pointed foot position greatly influences the variation of the knee moment $M_K$ and the ankle moment $M_T$. The angle between the lower leg shaft 4 and the prosthetic foot 6 is determined in order to detect the plantar flexion of the foot 6 relative to the lower leg shaft 4. This is required since the pointed foot position has a strong influence on the stability or instability of the prosthetic knee joint 3. By increasing the pointed foot angle with more plantar flexion, a hyper-extending moment is produced in the knee joint 3, having a stabilizing effect. In principle, a suboptimal set-back adjustment can be compensated by changing the pointed foot adjustment with the prosthetic knee joint 3 being extended very early with a great pointed foot angle. The required extension moment for initiating the swing phase is great and must be applied for a relatively long time. The extension element that is necessary to initiate the swing phase becomes smaller as the pointed foot angle becomes smaller, and setup of the extension moment is commenced later. The smaller the pointed foot angle, the smaller the extension moment necessary for initiating the swing phase and the later extension moment set up is commenced. The pointed foot angle also has an influence on the variation of the knee moment $M_K$ when the prosthesis 1 is under load, the aim of the pointed foot angle adjustment being to provide a variation of the knee moment $M_K$ that is as uniform as possible. The greater the pointed foot angle, the shorter the time during which the heel of the prosthetic foot 6 is under load.

Should it be found that the resultant force vector in the standing phase during walking is situated behind the joint axis 31 of the prosthetic knee joint 3, that is to say that there is an unstable setup in the standing phase, the joint axis 31 is adjusted or displaced until the resultant force vector extends in front of the joint axis 31 or until the joint axis 31 is arranged behind the resultant force vector. Apart from the knee joint axis 31, a joint axis 61 of the prosthetic foot 6 may also be displaced in order to achieve a stable prosthesis setup. In addition or as an alternative, an extension stop of the knee joint 3 and an extension stop of the foot joint 61, that is to say the dorsal stop, may be changed, in particular changed synchronously. The knee joint axis 31, the foot joint axis 61 and/or the extension stops 24, 46 may be adjusted so that the resultant force vector lies in front of the knee joint axis 31 during standing.

To be able to verify the adjustment of a prosthetic knee joint 3 during use, the normal distance λ of the resultant force vector $F_R$ is determined from the knee axis 31 at each point in time or sampling point during standing. To obtain the normal distance λ, the orientation and the point of attack of the resultant force vector $F_R$ or the ground reaction force $F_K$ are determined. Because only a displacement within the sagittal plane is considered for assessing whether the prosthesis setup during standing is in a stable or unstable state, a planar problem is concerned. It is possible to determine the resultant force vector $F_R$ or the corresponding contact force $F_K$ in its position and orientation from the ankle moment sensor 11 as well as the sensor for determining the axial force $F_{AX}$ and the sensor 10 for determining the knee moment $M_K$ as well as the previously determined lengths $H_S$ and $L_T$. Everything which happens above the knee joint 3 can thereby be reduced to the resultant force $F_R$, which means that no actively applied hip moments $M_H$ are taken into account and that the influence of a horizontal component of the ground reaction force $F_{GRF}$ on the ankle moment $M_T$ is negligible. The assumption that the hip moment $M_H$ is negligible can be correctly made if the prosthesis setup is not substantially unstable. To be able to take account of hip moments $M_H$, at least one further sensor would have to be provided.

The current hip moment $M_H$ is determined by determining the resultant force vector and the given geometry of the prosthesis 1. It is preferred that the prosthetic leg 1 have only small hip moments during the standing phase. If this is not the case, the moments in the two hip joints are not equal, causing horizontal forces to occur.

To be able to appraise the hip moment $M_H$, a calculation can be made with the determined contact force $F_K$ by way of the equilibrium of moments at the hip joint with $M_H=L_2 \times F_K$ and the relationship $L_2=L_F \sin(\phi-\alpha)+\lambda$, and with $L_F$ as the measured length of the upper leg and $L_2$ as the distance of the resultant force vector from the point of attack of the hip moment $M_H$ with the knee angle $\phi$. To be able to calculate the effective lever length $L_1$ at the height of the ankle moment sensor 5, the quotient of the measured ankle moment $M_T$ and the axial force $F_{AX}$ in the lower leg shaft 4 is formed. The lever length $L_1$ indicates the distance of the force entry point of the ankle joint at the height of the ankle moment sensor 11. The equilibrium of moments at the ankle joint is $M_T=-L_1 \times F_K$.

For the explicit calculation of the vertical component of the contact force $F_K$, the equation $M_T=F_{AX} \times L_1 - F_{KX} \times H_S$ is correspondingly resolved. The knee moment $M_K$ corresponds to the negative product from the normal distance $\lambda$ and the contact force $F_K$. The equilibrium of forces at the lower leg shaft 4 with $F_K \cos(\alpha)+F_{AX}=0$ and the geometric relationship $\sin(\alpha)=(\lambda-L_1)/L_T$ provides a nonlinear system of equations from which the values sought can be calculated.

In this case, the angle $\alpha$ is the angle between the force vector and the longitudinal axis of the prosthesis 1. $F_{KX}$ and $F_{KY}$ are contact force components in the x and y directions. The calculation of the required variables $F_{KX}$, $F_{KY}$, $L_1$ and $\lambda$ is performed in a computer into which the geometric variables and dimensions as well as the measured moments, angles and forces are entered. The current measured values can be sent into the computer by way of an interface and the dimensions can be entered manually. The fact that the normal distance $\lambda$ of the ground reaction vector $F_{GRF}$ or of the contact force vector $F_K$ from the knee axis 31 can be calculated at each point in time during standing means that it is also possible at each point in time of the standing phase to determine whether the prosthesis setup is stable or unstable. Whether the setup is stable or unstable can be established by a comparison of the determined distance with a defined distance for a stable, unstable or dynamic setup.

To further optimize the prosthesis setup, the pointed foot adjustment should be chosen such that the force vector while standing extends through the middle of the foot 6. This can be realized by means of a rocker arrangement, on which a person with the prosthesis 1 stands in such a way that the middle of the plate is located at the desired position of load introduction of the prosthetic foot 6. By means of a marking on the plate, the middle of the foot 6 can be brought over the turning point, the heel and toes having to be spaced at equal distances from the marking. When standing in a relaxed position, the plantar flexion can be changed until the plate is in equilibrium and rocks on a rod provided underneath the marking. As soon as equilibrium is reached, the point of origin of the force is in the middle of the foot 6.

Because changing the setup, in particular displacing the joint axis 31, joint axes 31, 61 or stops 24, 46, has the effect of changing the alignment of the prosthetic foot 6, the relative position of the prosthetic foot 6 is marked with respect to the lower leg shaft 4 before displacement of the joint axis 31. The prosthetic foot 6 is restored to the relative position with respect to the lower leg shaft 4 after displacement of the joint axis 31. This ensures that the geometric relationships that are changed by the adjustment of the joint axis 31 do not have any effect on the alignment of the prosthetic foot 6.

A simple method for marking and restoring the original adjustment of the prosthetic foot 6 includes determining the relative position of the prosthetic foot 6 with respect to the lower leg shaft 4 by a laser pointer being fixedly arranged on the upper leg shaft 2. A laser beam is directed onto the prosthetic foot 6 and the point of impingement is marked. After displacement of the joint axis 31, if the laser pointer is unchanged the prosthetic foot 6 is adjusted in such a way that the marking is made to coincide again with the laser beam. Instead of a laser pointer, other marking means, in particular optical marking means, may also be used.

After displacement of the joint axis 31 and alignment of the prosthetic foot 6, the plantar flexion of the prosthetic foot 6 may also be adjusted. Before displacement of the joint axis 31, a reference line is drawn from the upper leg shaft 2 to the prosthetic foot 6 and the prosthetic foot 6 is aligned in such a way to coincide again with the reference line to ensure that the prosthetic foot 6 is on a horizontal plane, as it originally was. If the reference line coincides with the axis of an adjusting core between the knee joint prosthesis 3 and the prosthetic foot 6, that is to say in the region of the ankle, an error in the shaft preflexion can be largely avoided. The reference line may be placed through a distal adjusting axis of the prosthetic knee joint 3.

After adjusting the plantar flexion adjustment, measuring the moments and forces within the prosthesis 1 and determining the character of the prosthesis setup, the joint axis 31 is displaced to the front or to the rear in the sagittal plane by an amount $\lambda'$. The necessary displacement $\lambda'$ to achieve a target moment of M' in the knee joint 3 while standing flexion can be calculated. Alternatively, the displacement may take place by changing the extension stops in the opposite direction by arctan $(\lambda'/L_T)$.

Figure 5A:
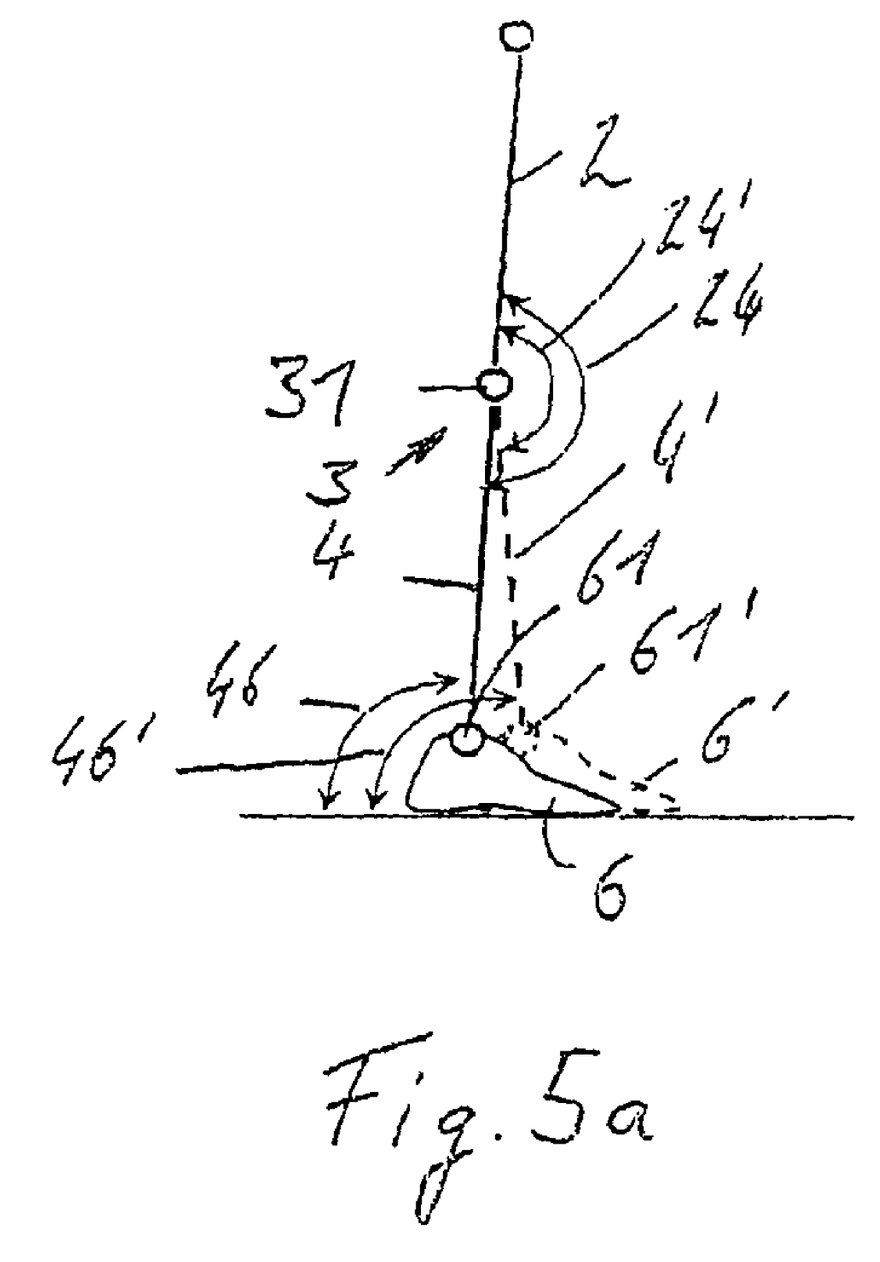
FIG. 5a shows a schematic representation of an adjustment of extension stops.

Shown in FIG. 5a is a schematic representation of a leg prosthesis 1 in which the upper leg shaft 2 is connected to the lower leg 4 by means of the prosthetic knee joint 3 with the joint axis 31. The lower leg 4 bears at its distal end a prosthetic foot 6, which is pivotable by means of a joint axis 61 to the lower leg shaft 4. In an exemplary embodiment, the prosthetic foot 6 is adjustably connected to the lower leg shaft 4. There is an adjustable extension stop 24 between the lower leg shaft 4 and the upper leg shaft 2, which is indicated by an arrow. This extension stop 24 can be changed, for example, in such a way that the prosthetic foot 6 is displaced further forward. The prosthetic foot 6 is then in the position 6' shown by dashed lines, while the lower leg shaft 4' is pivoted forward in the walking direction. The extension stop 24' taken up by the knee joint 3 is adapted to realize a stable or dynamic setup depending on the determined position of the resultant force vector. At the same time, the dorsal stop 46 of the prosthetic foot 6 can either be adjusted synchronously, in which case the dorsal stop 46' brings about an adaptation of the position of the prosthetic foot 6. The adjustment of the extension stops 24, 46 may take place under electronic control by means of actuators, for example lockable hydraulic cylinders. Consequently, an adaptation to different prosthesis users or different operating conditions can be performed. It is likewise possible that, when there is a displacement of the lower leg 4 in relation to the joint axis 31, the position of the prosthetic foot 6 is automatically corrected so that a prosthesis setup according to the requirements envisioned by the prosthesis user can be realized depending on the existing prosthesis setup, the operating conditions and the position of the prosthesis 1 on the prosthesis user.

If the dorsal stop 46 of the foot joint 61 and the extension stop 24 of the knee joint 3 are adjusted oppositely in relation to each other, the flexion of the upper connection or upper leg shaft 2 is changed, which does not lead to corresponding results in comparison with a displacement of the axes of rotation. The flexion of the upper leg shaft 2 can be used to distinguish between standing and walking. Therefore, an iterative evaluation process is carried out to determine the setup, a process in which the position of the resultant force vector in relation to the joint axis 31 is determined and the prosthesis setup is changed until a sufficiently stable setup in the standing phase in the course of the walking cycle is achieved. If the prosthesis user would like a dynamic setup, the prosthesis 1 is adjusted in such a way that the force vector extends directly in front of the joint axis 31. However, the method and the setup adjusting system show where the force vector extends so that a qualified and quantitatively recorded, possibly documented, adjustment of the prosthetic knee joint 3 can be performed.

The knee joint axis 31, the foot joint axis 61 and/or the extension stops 24, 46 may be adjusted so that the resultant force vector lies in front of the knee joint axis 31 during standing.

In particular, in the case of electronically controlled knee joints or foot joints, displacement of the joint axes 31 or 20 changing of the extension or dorsal stops 24, 46 can be effectively used by distinguishing between walking and standing. During walking, it is desired to have a set-back displacement that is as small as possible in order to minimize the expenditure of force; during standing, it is desired to have a stable set-back displacement in order to ensure a stable prosthesis setup and stable standing. The currently active moments are determined by means of ankle moment and knee moment sensors 10, 11. Adjustable stops, for example arrestable hydraulic cylinders with corresponding actuators, adjust the optimum position of the joint axes 31 or of the stops 24, 46 depending on the measured moments and the determined vector position. The position to be adopted is prescribed on the basis of empirical data or personal preference of the prosthesis user.

Figure 6:
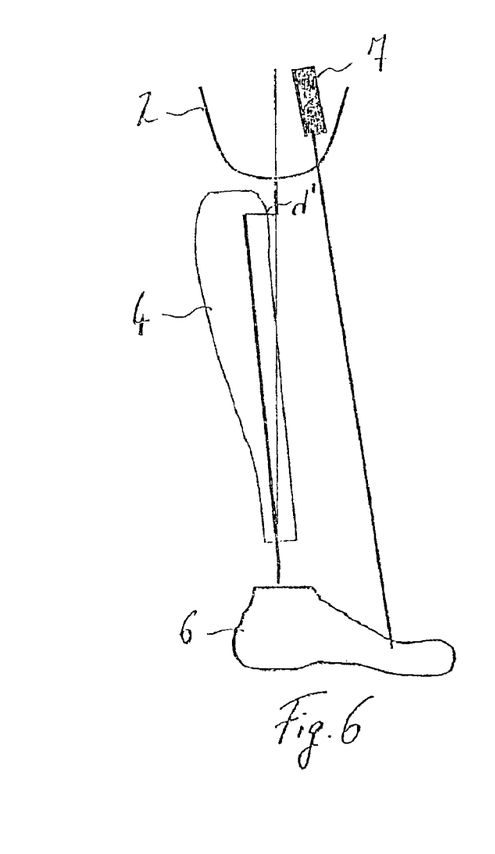
FIG. 6 shows a schematic representation of the restoration of the foot position.

To align the position of the prosthetic foot 6 after an adaptation of the set-back displacement by adjustment of the knee axis 3, a light spot is applied to the upper side of the prosthetic foot 6 and marked by means of a laser pointer 7 fastened to the upper leg shaft 2 before the adjustment, as shown in FIG. 6. Subsequently, the joint axis 3 is displaced by the calculated amount λ'. After displacement, the prosthesis 1 is turned until the projected point coincides again with the marking.

Before the set-back displacement, the pointed foot adjustment or plantar flexion of the prosthetic foot 6 should be checked. This preferably takes place after alignment of the prosthetic foot 6 as described above by means of a laser pointer. When restoring the original plantar flexion, screws on an ankle pyramid 9 are loosened with the user of the prosthesis 1 standing comfortably so that the system can settle and the sole of the shoe rests flat on the ground. The screws are then tightened again. Alternatively, to adjust the plantar flexion, the rocker described above may be used or a continuous reference line 9 may be drawn on the lower leg shaft 4 and the prosthetic foot 6 before the set-back displacement. After the set-back displacement, the parts offset from the line are brought into line with one another so that the original pointed foot adjustment is restored. After displacement of the first set-back, alignment of the prosthetic foot 6 and plantar flexion correction, the prosthesis setup is evaluated once again over a number of step cycles on a level surface and corrected.

Finally, the maximum loads occurring are checked. If a satisfactory adjustment has been found, the moment sensor 10 in the prosthetic knee joint 3 can be replaced by a suitably adjusted displacing adapter.

Figure 8:
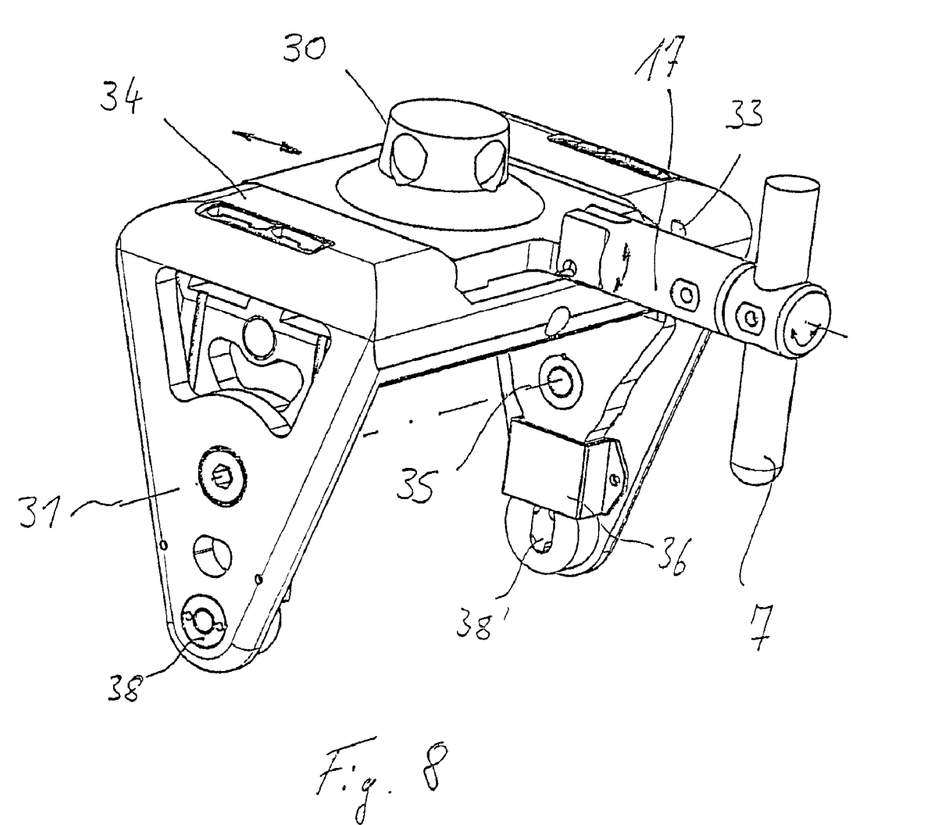
FIG. 8 shows an exemplary embodiment of the apparatus according to the invention in the assembled state.

The moment sensor 10 is in this case advantageously set up according to FIG. 8, in which a pyramid socket 30 for introduction into the upper leg shaft 2 is arranged. The pyramid socket 30 is fixed in a desired position on a carrier 34 by means of a clamping device 32, which is represented in detail in FIG. 10. As indicated by the double-headed arrows, the pyramid socket 30 is displaceable along the axis of the arrows with the pyramid socket 30 being held stationary in the longitudinal direction by means of a wedge guide. Arranged on the pyramid socket 30 is a holder 17 for a laser pointer 7. The laser pointer 7 and the holder 17 are ventrally arranged with the holder 17 being pivotally mounted about an axis of rotation in the transversal plane. Likewise, the laser pointer 7 may be turned about an axis in the sagittal plane by its mounting. The clamping device 32 can be released and locked by means of clamping screws 39', which are accessible through bores 33 lying in the sagittal plane so that the pyramid socket 30 can be displaceably fixed on the carrier 34. The pyramid socket 30, the carrier 34 and the bridge element 35 form the connecting means for fastening the upper part (not represented) of the prosthetic knee joint 3 to the upper leg shaft 2.

Figure 9:
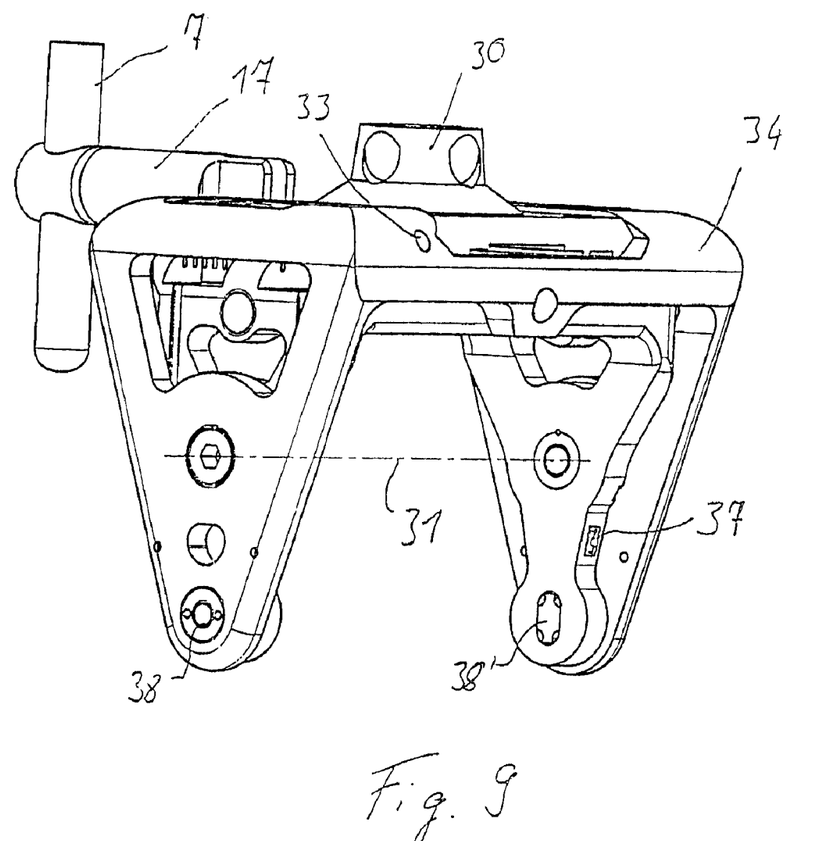
FIG. 9 shows a variant of FIG. 8 in a turned position.

A refinement of the invention provides a bridge element 35 and/or a carrier arranged between the upper part (not represented) of the knee joint 3 and the adapter. For this purpose, a turning joint 38 and a sliding joint 38' are formed at the connection to the upper part of the prosthesis 1. The turning joint 38 permits turning based on elastic deformations, while the sliding joint 38' allows linear compensation, and consequently prevents longitudinal stresses. The mounting on the upper part is arranged below the axis of rotation 31. The adapter is displaceably mounted on the bridge element 35 and/or a carrier. The bridge 35 or the carrier is in this case fastened to the upper part in a preferably moment-resistant manner and forms an intermediate piece which is situated between the adapter arranged directly on the upper leg shaft 2 and the upper part and is appropriately designed for determining the forces and moments that are effective in the knee joint 3. The bridge element 35 forms a measuring beam and, for reasons of space, is aligned with the open limbs distally disposed. When subjected to moments or forces, the measuring beam deforms to such a degree that the effective knee forces and knee moments can be clearly determined with a high measuring signal, for example strain gages 37, provided on the bridge element 35, as shown in FIG. 9. In FIG. 8, the strain gages 37 are protected by a protective cover 36. This provides an inexpensive refinement of a bidirectional measuring unit. However, the measuring beam must be dimensioned in such a way that the bridge 35 does not fail and the structure remains intact even when maximum load values are reached. The adapter or the adapter with the bridge 35 and/or the carrier are preferably designed in such a way that the fitting height corresponds to the fitting height of the connecting means that is used after the adjustment of the prosthesis setup. In the case of this variant, it is provided that, once the optimum prosthesis setup has been determined, the device is removed and replaced by the normal connecting means.

FIG. 9 shows a rear view of the moment sensor with the strain gages 37, which are arranged between the joint axis 31 and the sliding joint 38' or turning joint 38.

Figure 10:
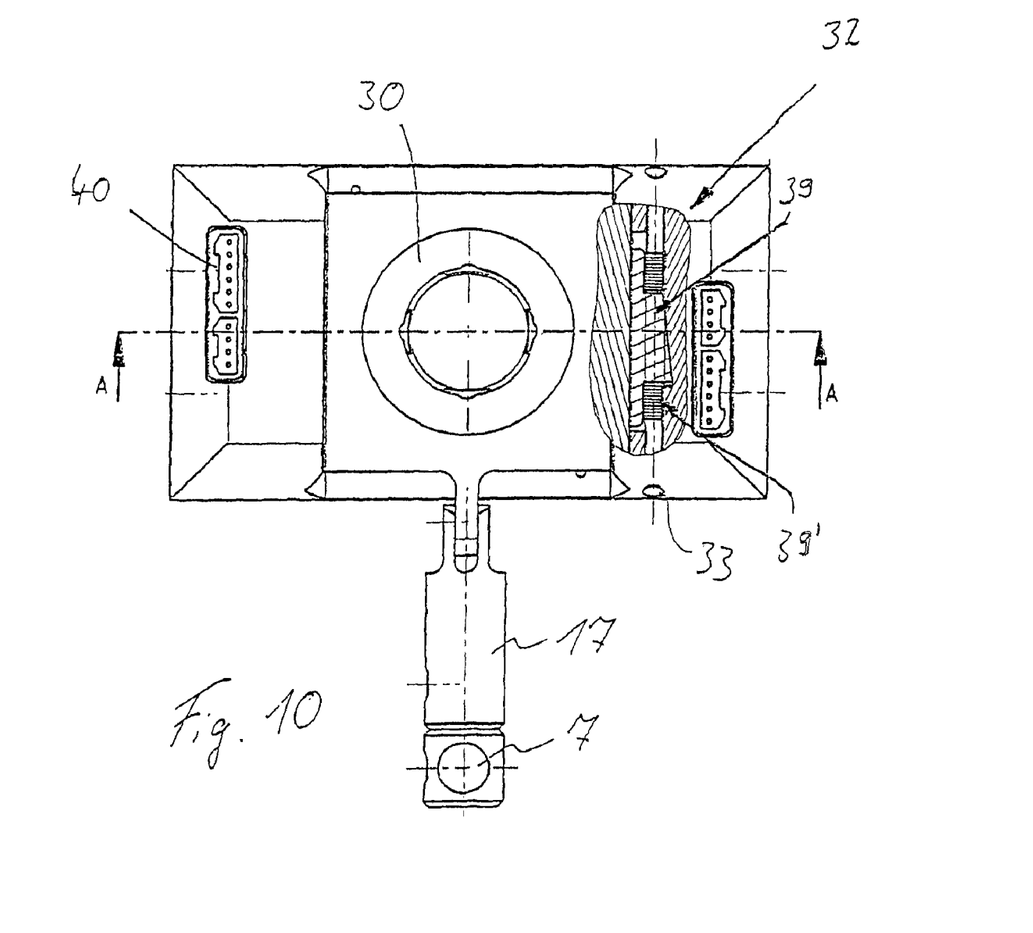
FIG. 10 shows a plan view of the apparatus.

Shown in plan view with partial detail in FIG. 10 is the clamping device 32, which displaces a clamping wedge 39 by means of clamping screws 39'. If the clamping screw 39' assigned to the laser pointer 7 is screwed in, a force is exerted in the direction of the frontal plane by way of the clamping wedge 39, whereby the pyramid socket 30, which is formed here as a displacing adapter, is fixed on the carrier 34. A reverse turning movement of the clamping screw 39' has the effect that the clamping wedge 39 is made to move in the other direction, and the clamping is accordingly released. The clamping screw 39' is in this case formed in such a way that access is possible from both sides. It is possible by appropriate mounting of the clamping screw 39' that both opening and closing the fixing or clamping are possible from both sides.

Figure 11:
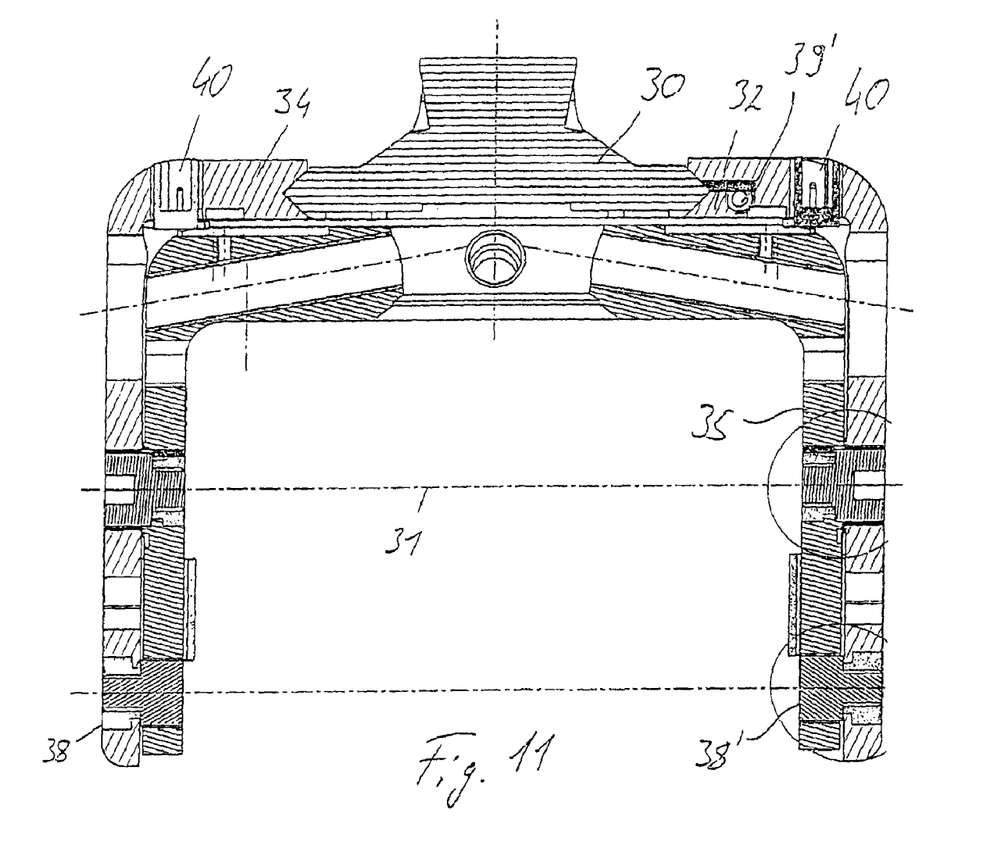
FIG. 11 shows a sectional representation along A-A of FIG. 10.

Connectors 40 or interfaces, which permit the reading out of sensor data and transmission to an evaluation device, for example a computer, are formed on the upper side of the holder 34. A section A-A, which is taken in the frontal plane, is represented in FIG. 11. In this section, the wedge guide of the pyramid socket 30 in the carrier 34 can be seen, as can the clamping device 32 with the clamping screw 39' and the interfaces 40 with respect to a computer.

Once evaluation of the prosthesis setup has taken place, the entire apparatus for detecting the knee moments $M_K$, with the pyramid adapter 30, the carrier 34, the bridge element 35 and the strain gages 37, can be exchanged for conventional adapters for fastening the prosthetic knee joint 3 to the upper leg shaft 2. For this purpose, the dimensions of the apparatus are made to be similar to those of the conventional adapters. It is also possible to always use the apparatus represented by the measured values constantly being evaluated by a computer and possibly evaluated for controlling damper devices. In the case of an envisioned exchange, the is are transmitted by way of the interfaces 40 to a computer, which calculates over which path a displacement of the pyramid adapter 30 must take place in relation to the joint axis 31 in order that a stable, neutral or dynamic setup is achieved. The degree of adjustment or the present fitting situation can be output on a display.

As an alternative to the embodiment represented, other knee moment sensors may also be provided and used.

The invention claimed is:

1. A method for verifying the adjustment of a leg prosthesis, wherein the leg prosthesis includes a prosthetic knee joint pivotally connected to an upper connection and a lower leg shaft, wherein the upper connection fixes the leg prosthesis on a user of the leg prosthesis and the lower leg shaft fastens to a prosthetic foot, and wherein the upper connection is displaceable in relation to a joint axis of the prosthetic knee joint, the method comprising:
measuring a knee moment and an axial force by means of sensors when the leg prosthesis is being used;
calculating a resultant force vector using the knee moment and the axial force;
calculating a normal distance relative to the joint axis and the position of the resultant force vector in relation to the joint axis; and
verifying a position of the resultant force vector relative to the joint axis in the sagittal plane.

2. The method of claim 1, further comprising calculating the resultant force vector with a point of attack on the upper connection.

3. The method of claim 2, wherein calculating the resultant force vector with a point of attack comprises calculating the resultant force vector from a quotient of an ankle moment and an axial force in the lower leg shaft.

4. The method of claim 1, further comprising determining the normal distance of the resultant force vector from the joint axis.

5. The method of claim 1, further comprising detecting an ankle moment by means of an ankle moment sensor, wherein the resultant force vector is determined with inclusion of the ankle moment, the knee moment, the axial force and a length of the lower leg shaft.

6. The method of claim 5, wherein determining the axial force, knee moment and ankle moment comprises using the data from the sensors, from which a vector of the ground reaction force in the sagittal plane is determined.

7. The method of claim 1, wherein measuring the knee moment and the axial force occur during walking.

8. The method of claim 1, further comprising determining the current knee angle and/or the upper leg angle in relation to the vertical line to determine a resultant force vector.

9. The method of claim 1, further comprising determining an angle between the lower leg shaft and the prosthetic foot, wherein the knee moment and/or an ankle moment are calculated based on detection of the angle.

10. The method of claim 1, wherein when the resultant force vector is positioned behind the joint axis during a standing phase, the joint axis is displaced to behind the resultant force vector.

11. The method of claim 10, further comprising:
marking a relative position of the prosthetic foot with respect to the lower leg shaft before displacing the joint axis; and restoring the relative position of the prosthetic foot with respect to the lower leg shaft after displacement of the joint axis.

12. The method of claim 11, further comprising fixing the relative position of the prosthetic foot by a laser beam being directed onto the prosthetic foot by means of a laser pointer fixedly arranged on the upper leg shaft, wherein a point of impingement marked and the marking on the prosthetic foot are aligned with the laser beam after displacement of the joint axis.

13. The method of claim 10, further comprising correcting a plantar flexion adjustment of the prosthetic foot after the displacement of the joint axis.

14. The method of claim 13, further comprising drawing a reference line from the lower leg shaft on the prosthetic foot and the lower leg shaft before displacing the joint axis to correct the position of the plantar flexion of the prosthetic foot before displacing the joint axis.

15. The method of claim 14, further comprising aligning the prosthetic foot such that the reference line coincides with the joint axis after displacing the joint axis.

16. The method of claim 14, wherein drawing the reference line comprises placing the reference line through an adjusting axis of the prosthetic knee joint.

17. The method of claim 1, further comprising determining a current hip moment by determining the resultant force vector and a given geometry of the prosthesis.

18. A method for adjusting a leg prosthesis having a prosthetic knee joint pivotally connecting an upper connection for fixing the leg prosthesis on a prosthesis user and a lower leg shaft to which a prosthetic foot is fastened, wherein the upper connection is displaceable in relation to a joint axis of the prosthetic knee joint and/or the position of the prosthetic foot in relation to the lower leg shaft, the method comprising:
measuring a knee moment and an axial force by means of sensors when the prosthesis is being used;
calculating a resultant force vector using the knee moment and the axial force;
calculating a normal distance in relation to the joint axis and the position of the resultant force vector in relation to the joint axis;
verifying a position of the resultant force vector relative to the joint axis in a sagittal plane; and
adjusting the upper connection in relation to an axis of the prosthetic knee joint and/or extension stops for the prosthetic knee joint and/or a prosthetic foot joint based on the position of the resultant force vector.

19. The method of claim 18, wherein adjusting the upper connection comprises adjusting a knee joint axis, a foot joint axis, and/or an extension such that the resultant force vector lies in front of the knee joint axis when standing.

20. An apparatus for measuring forces or moments in a leg prosthesis having a prosthetic joint comprising:
- an upper part connectable to an upper connection for fastening to a user of the prosthesis;
- a lower part jointly connected to the upper part;
- connecting means for fastening the upper part to the upper connection; and
- means for detecting knee forces or moments provided on one of the connecting means and the upper part, wherein the detected knee forces or moments are used to verify an adjustment of the leg prosthesis.

21. The apparatus of claim 20, wherein the connecting means has an adapter mounted displaceably in a sagittal plane on the upper part.

22. The apparatus of claim 21, wherein the adapter is fixed on a holder by a clamping device.

23. The apparatus of claim 21, further comprising a carrier and/or bridge element arranged between the upper part and the adapter, wherein the adapter is displaceably mounted on the carrier and the carrier is fixed to the upper part.

24. The apparatus of claim 23, further comprising a strain gage for determining effective knee forces and moments provided on the bridge element.

25. The apparatus of claim 21, wherein the adapter has a fitting height that corresponds to a fitting height of the connecting means that is used after adjustment of the prosthesis setup.

26. The apparatus of claim 20, further comprising a carrier for a marking device fastenable to the connecting means.

27. The apparatus of claim 20, wherein the upper connection is formed as an upper leg shaft.

* * * * *